(12) United States Patent
Gibson

(10) Patent No.: US 6,974,457 B2
(45) Date of Patent: Dec. 13, 2005

(54) ABLATION CATHETER

(75) Inventor: Charles A. Gibson, Malden, MA (US)

(73) Assignee: C.R. Bard Inc., Murray Hill, NJ (US)

( * ) Notice: Subject to any disclaimer, the term of this patent is extended or adjusted under 35 U.S.C. 154(b) by 0 days.

(21) Appl. No.: 10/250,854

(22) PCT Filed: Jan. 4, 2002

(86) PCT No.: PCT/US02/00076

§ 371 (c)(1),
(2), (4) Date: Jan. 14, 2004

(87) PCT Pub. No.: WO02/060332

PCT Pub. Date: Aug. 8, 2002

(65) Prior Publication Data

US 2004/0225285 A1    Nov. 11, 2004

Related U.S. Application Data

(60) Provisional application No. 60/261,016, filed on Jan. 11, 2001.

(51) Int. Cl.$^7$ .............................................. A61B 18/14
(52) U.S. Cl. ........................ 606/41; 600/374; 607/122
(58) Field of Search ......................... 600/374; 606/41; 607/122

(56) References Cited

U.S. PATENT DOCUMENTS

| | | | | |
|---|---|---|---|---|
| 4,328,812 A | * | 5/1982 | Ufford et al. | ................ 607/122 |
| 4,559,951 A | * | 12/1985 | Dahl et al. | .................. 600/374 |
| 5,257,635 A | | 11/1993 | Langberg | |
| 5,472,441 A | | 12/1995 | Edwards et al. | |
| 5,545,161 A | | 8/1996 | Imran | |

* cited by examiner

*Primary Examiner*—Lee S. Cohen
(74) *Attorney, Agent, or Firm*—Darby & Darby

(57) ABSTRACT

An ablation catheter comprises a shaft and at least one ablation electrode which may be fixed or movable relative to the shaft. An insulating cap is placed over portions of the electrode which are susceptible to high current concentrations when RF energy is applied to the electrode. Typically, such portions occur in the region of abrupt surface transitions such as the edges of the electrode.

3 Claims, 1 Drawing Sheet

FIG. 1
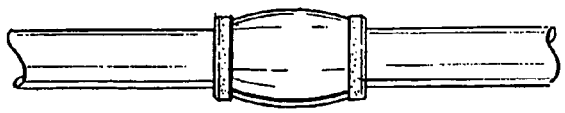
FIG. 2
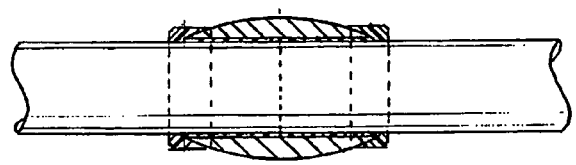
FIG. 3
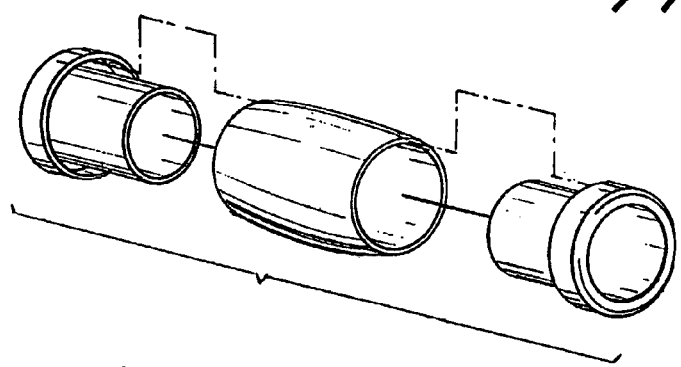
FIG. 4
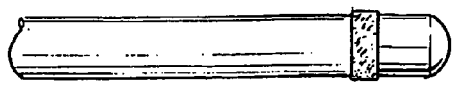
FIG. 5
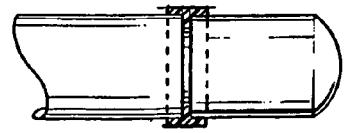
FIG. 6

ABLATION CATHETER

CROSS-REFERENCE TO RELATED APPLICATIONS

This application is a 371 of PCT/US02/00076 filed Jan. 4, 2002, which claims the priority of U.S. Provisional Application No. 60/261,016, filed on Jan. 11, 2001 entitled "Ablation Electrode Cap" which is hereby incorporated by reference in its entirety.

FIELD OF THE INVENTION

The present invention relates generally to the field of cardiac ablation. More particularly, this invention relates to an ablation catheter which can be used for cardiac ablations wherein the risk of adverse effects such as blood coagulation is reduced.

BACKGROUND OF THE INVENTION

Cardiac arrhythmias are the result of various defects in the heart. One such defect is an extraneous stand of muscle fibre in the heart that provides an abnormal short circuit pathway for electric impulses traveling through the heart tissue. This accessory pathway often causes the electric impulses that normally travel from the upper to the lower chamber of the heart to be fed back to the upper chamber, causing the heart to beat irregularly and therefore inefficiently pump blood.

Another common type of cardiac arrhythmia is ventricular tachycardia (VT), which may be a complication resulting from a heart attack or from a temporary reduction of blood supply to an area of heart muscle. VT is often caused by a tiny lesion, typically on the order of 1–2 mm, that is located close to the inner surface of the heart chamber. That lesion is often referred to as an "active site" because it does not fire in sequence with the rest of the heart muscle. VT causes the heart's normal rhythmic contraction to be altered, thereby affecting heart function. A typical symptom is rapid, inefficient heartbeats. Minimally invasive techniques have been developed which are used to locate cardiac regions responsible for the cardiac arrhythmia, and also to disable the short-circuit function of these areas. According to these techniques, electrical energy shocks are applied to a portion of the heart tissue to ablate that tissue and produce scars which interrupt the reentrant conduction pathways. The regions to be ablated are usually first determined by endocardial mapping techniques. Mapping typically involves the percutaneous introduction of a diagnostic catheter having one or more electrodes into the patient, passing the diagnostic catheter through a blood vessel (e.g. the femoral vein or aorta) and into an endocardial site (e.g., the atrium or ventricle of the heart), and inducing a tachycardia so that a continuous, simultaneous recording can be made with a multichannel recorder at each of several different endocardial positions. When a tachycardia focus is located, as indicated in the electrocardiogram recording, it is marked by means of a fluoroscopic image so that cardiac arrhythmias at the located site can be ablated. An ablation catheter with one or more electrodes can then provide electrical energy to the tissue adjacent the electrode to create a lesion in the tissue. One or more suitably positioned lesions will create a region of necrotic tissue to disable the malfunction caused by the tachycardia focus.

Ablation is carried out by applying energy to the catheter electrodes once the electrodes are in contact with the cardiac tissue. The energy can be, for example, RF, DC, ultrasound, microwave, or laser radiation. When RF energy (e.g. 510 $KH_z$) is delivered between the distal tip of a standard electrode catheter and a backplate, there is a localized RF heating effect. This creates a well-defined, discrete lesion slightly larger than the tip electrode (i.e., the "damage range" for the electrode), and also causes the temperature of the tissue in contact with the electrode to rise.

Radio frequency ablation catheters are available with different types of ablation electrodes. These electrodes have different diameters and profiles depending on the intended therapeutic application, the anatomic location of the electrode, and the efficiency by which the RF energy is transmitted from the electrode in the form of heat. It is known that the current in an electrode associated with RF energy tends to have greater concentrations where the surface of the electrode is less continuous, i.e. less smooth. Such surface areas generally have an abrupt transition such as an edge. This higher concentration of electrical current can result in unequal heating at the surface of the electrode due to the nonuniform distribution of energy. At about 100° C., charring and desiccation occur which significantly changes the electrical conductivity of blood and tissue, causing an increase in the overall impedance of the electrical heating circuit and thus a diminution in the power delivered to the tissue. Charring is particularly troublesome because of the possibility that the char may be dislodged from the electrode and enter the blood stream causing serious adverse effects for the patients. When charring occurs, the electrode must be removed and cleaned before the procedure can continue.

In conventional RF ablation catheters, the electrode is provided with a temperature sensing element which is used to control the energy fed to the electrode. This system works if the sensor is placed properly at the most likely site on the electrode surface where hot spots are likely to occur. If multiple hot spots are possible, multiple temperature sensors are needed. As electrodes become more complex, the need to use multiple temperature sensors becomes a limiting factor both from the viewpoint of cost and performance and may result in compromises in electrode design to minimize the appearance of hot spots due to electrical current concentration.

Accordingly, it is an object of the invention to provide an RF ablation catheter which is less likely than prior art electrode catheters to cause charring.

A more specific object of the invention is to provide an RF ablation catheter wherein multiple temperature sensors are not required to avoid the creation of hot spots which can lead to charring.

SUMMARY OF THE INVENTION

Briefly, in accordance with the invention, an RF ablation catheter comprises a catheter shaft to which one or more electrodes is connected. The electrodes may be movable or stationary and of any design. An insulative cap is applied to those portions of the electrode where current is likely to concentrate and cause hot spots. Typically, such areas consist of the edge or edges of the electrode.

DESCRIPTION OF THE DRAWINGS

FIG. 1 is a side elevation showing an RF ablation catheter having a movable electrode in accordance with the invention;

FIG. 2 is a side sectional view showing the RF ablation catheter of FIG. 1;

FIG. 3 is an exploded perspective view showing the electrode and end caps;

FIG. 4 is a side elevation showing an RF ablation catheter having a fixed tip electrode in accordance with the invention;

FIG. 5 is an exploded perspective view of the distal tip electrode shown in FIG. 4; and FIG. 6 is a side sectional view of the electrode construction shown in FIGS. 4 and 5.

DETAILED DESCRIPTION

As indicated above, the invention has utility with many different types of electrode configurations. FIGS. 1, 2 and 3 illustrates a configuration in which the electrode 10 is movable with respect to a catheter shaft 12. The mechanism for moving the electrode may be conventional and, therefore, is not illustrated. Likewise, the electrical wires which connect the electrode to the RF equipment at the side of the patient are not shown. Simultaneously, it is contemplated that a conventional temperature sensor will be included in the electrode to control the temperature of the electrode.

The electrode has a smooth bowed surface with abrupt surface transitions at the proximal and distal edges 18 and 20, respectively. Because of these abrupt transitions, when the electrode is energized, current tends to concentrate at these edges. This can cause excessive heating at the electrode/tissue interface, which can lead to hot spots and charring as described above. In accordance with the invention, proximal and distal insulated sleeves 24 and 26, respectively, are provided at the ends of the electrode. Each of the sleeves includes a cylindrical collar 28 which fits between the outer surface of the shaft 12 and the inner surface of the annular electrode 10. At the exposed extremity of each sleeve an annular cuff 30 engages the edge of the electrode 10 when the sleeves are fully inserted between the shaft and the electrode.

With this construction, the cuffs 30 function as insulators which prevent current flow to the tissues in those areas of the electrode (ends 18 and 20) where current tends to form hot spots.

FIGS. 4, 5 and 6 show a different ablation catheter in which a stationary electrode 32 is positioned at the distal tip of the catheter. The basic electrode construction also is conventional. In this case, an insulating sleeve 34 engages the proximal end of the electrode and the distal end of the shaft thereby covering the edge 36 of the electrode. In both cases, the operation of the insulative sleeve is essentially the same.

In the preferred embodiment, the insulative cap is adhered to the electrode by an adhesive. For example a two part epoxy system suitable for bonding the metallic electrode to the plastic shaft may be used. The parts could also be attached mechanically, for example by a plug-in type of system or by means of a threaded connection.

The insulative cap can be made of any electrically insulating material, for example, tfe Teflon or, possibly, polyetheretherketon (PEEK). Polyimide based materials have high electrical insulative values and can also be used but such materials have higher friction coefficients which is undesirable in the case of a movable electrode. The insulative properties of a selected material can be varied by changing thickness.

It is also contemplated that in some situations the insulative cap may cover the entire surface of the electrode. In this case, the cap may be made of a partially conductive material (for example, a plastic containing a metallic filler) which would dissipate the energy while preventing blood from contacting the hot spots in the electrode.

The effect of the insulating cap, in accordance with the invention, is to provide a more uniform temperature along the surface of the electrode. Thus, an added benefit of the invention is providing greater flexibility in the placement of temperature sensors since the electrode surface temperatures are more uniform along the electrode/tissue interface.

What is claimed is:

1. An ablation catheter comprising a shaft and at least one ablation electrode connected to said shaft and means for applying RF energy to said electrode, the improvement comprising:
   an insulative covering covering a portion of such electrode which is susceptible to high current concentration when RF energy is applied to said electrode;
   said electrode including distal and proximal edges;
   said insulative covering comprising a plastic cap covering each of said edges and wherein each plastic cap includes a collar which envelopes the shaft; and
   said electrode being moveable with respect to said shaft.

2. An ablation catheter comprising a shaft and at least one ablation electrode connected to said shaft for connection to means for applying RE energy to said electrode, and with an insulative covering covering a portion of said electrode which is susceptible to high current concentration when RE energy is applied to said electrode, characterized in that said insulating covering comprises an insulative sleeve at each end of the electrode with each said sleeve having a collar which fits between the shaft and the electrode and also having a cuff which engages the respective edge of the electrode when the collar is fully inserted between the shaft and the electrode.

3. An ablation catheter as in claim 2, wherein said electrode is movable with respect to the shaft.

* * * * *